(12) United States Patent
Dallerup Rasmussen et al.

(10) Patent No.: US 11,567,090 B2
(45) Date of Patent: Jan. 31, 2023

(54) ARRANGEMENT, CASSETTE AND SERVICE MODULE FOR BIOMARKER ANALYSIS OF A MILK SAMPLE

(71) Applicant: DELAVAL HOLDING AB, Tumba (SE)

(72) Inventors: Claus Dallerup Rasmussen, Tumba (SE); Per Sonnich Thomsen, Tumba (SE)

(73) Assignee: DeLaval Holding AB, Tumba (SE)

( * ) Notice: Subject to any disclaimer, the term of this patent is extended or adjusted under 35 U.S.C. 154(b) by 325 days.

(21) Appl. No.: 16/623,342

(22) PCT Filed: Jun. 18, 2018

(86) PCT No.: PCT/SE2018/050639
§ 371 (c)(1),
(2) Date: Dec. 16, 2019

(87) PCT Pub. No.: WO2018/236271
PCT Pub. Date: Dec. 27, 2018

(65) Prior Publication Data
US 2021/0148941 A1    May 20, 2021

(30) Foreign Application Priority Data

Jun. 20, 2017  (SE) .................................... 1750790-6

(51) Int. Cl.
*G01N 35/00* (2006.01)
*B01L 3/00* (2006.01)
(Continued)

(52) U.S. Cl.
CPC ...... *G01N 35/00009* (2013.01); *A01J 5/0131* (2013.01); *A01J 5/0134* (2013.01);
(Continued)

(58) Field of Classification Search
None
See application file for complete search history.

(56) References Cited

U.S. PATENT DOCUMENTS 5,077,010 A    12/1991  Ishizaka et al.
5,096,828 A *  3/1992  Ishizaka ........... G01N 35/00009
                                                              422/66
(Continued)

FOREIGN PATENT DOCUMENTS

CN    102084247 A    6/2011
CN    102841594 A    12/2012
(Continued)

OTHER PUBLICATIONS

International Search Report and Written Opinion, dated Oct. 18, 2018, from corresponding PCT application No. PCT/SE2018/050639.

(Continued)

*Primary Examiner* — P. Kathryn Wright
(74) *Attorney, Agent, or Firm* — Nixon & Vanderhye

(57) ABSTRACT

An arrangement is provided that is configured to measure a biomarker value of an animal milk sample, including a cassette including a carrier tape having test zones indicating the biomarker value, and an inspective window. The carrier tape is disposed on first and second spools configured to cooperate with a cassette external motor. The arrangement also includes a service module including a camera configured to inspect the test zone, a motor configured to be engaged with a cassette spool, and a tube element configured to provide the milk sample to the test zone.

11 Claims, 6 Drawing Sheets

(51) Int. Cl.
  *G01N 35/02* (2006.01)
  *A01J 5/013* (2006.01)
  *G01N 33/04* (2006.01)

(52) U.S. Cl.
  CPC ............ *B01L 3/5082* (2013.01); *G01N 33/04* (2013.01); *G01N 35/021* (2013.01); *G01N 2035/00019* (2013.01)

(56) References Cited

U.S. PATENT DOCUMENTS

| | | | |
|---|---|---|---|
| 6,814,025 | B2 | 11/2004 | Chen et al. |
| 2002/0124803 | A1 | 9/2002 | Chen et al. |
| 2006/0260939 | A1 | 11/2006 | Anderson et al. |
| 2006/0285430 | A1 | 12/2006 | Seto |
| 2007/0217950 | A1 | 9/2007 | Kramer et al. |
| 2013/0319336 | A1 | 12/2013 | Thompson |
| 2019/0082659 | A1 | 3/2019 | Mottram |
| 2021/0185972 | A1* | 6/2021 | Gavin .............. G01N 35/00009 |
| 2021/0195863 | A1* | 7/2021 | Gavin .............. G01N 35/00009 |
| 2021/0259194 | A1* | 8/2021 | Dessing ........... G01N 35/00009 |
| 2021/0308683 | A1* | 10/2021 | Gavin .................... G01N 33/04 |
| 2021/0315181 | A1* | 10/2021 | Knip ....................... G01N 33/04 |
| 2021/0329877 | A1* | 10/2021 | Dessing ................ A01J 5/0135 |
| 2021/0341447 | A1* | 11/2021 | Gavin ....................... A01J 5/00 |
| 2021/0345576 | A1* | 11/2021 | Dessing ........... G01N 35/00009 |

FOREIGN PATENT DOCUMENTS

| | | |
|---|---|---|
| CN | 205982305 U | 2/2017 |
| EP | 0299517 A2 | 1/1989 |
| JP | H04-112785 A | 4/1992 |
| JP | H11-230970 A | 8/1999 |
| JP | 2006-349638 A | 12/2006 |
| JP | 2007-139770 A | 6/2007 |
| JP | 2007-532881 A | 11/2007 |
| JP | 2014-109455 A | 6/2014 |
| WO | 02/069697 A1 | 9/2002 |
| WO | 2004/034063 A2 | 4/2004 |
| WO | 2005/100539 A2 | 10/2005 |
| WO | 2013/032386 A1 | 3/2013 |
| WO | 2017/144913 A1 | 8/2017 |

OTHER PUBLICATIONS

SE Search Report, dated Jan. 5, 2018, from corresponding SE application No. 1750790-6.

Office Action issued in Chinese Patent Application No. 201880033478.0 dated Dec. 29, 2021.

Office Action issued in Japanese Patent Application No. 2019-558677 dated May 6, 2022.

* cited by examiner

ARRANGEMENT, CASSETTE AND SERVICE MODULE FOR BIOMARKER ANALYSIS OF A MILK SAMPLE

TECHNICAL FIELD

This document discloses an arrangement, a cassette and a service module. More particularly, an arrangement, a cassette and a service module are described, for measuring at least one biomarker value of a milk sample of an animal.

BACKGROUND

On an animal farm, it is important to keep the animals healthy in order to enhance milk/meat production. On a dairy farm, for example, it is very important to inseminate animals at an optimal moment in order to successfully fertilise the cow. It is important to find the right moment to inseminate each individual animal in the farm, for efficiency reasons. In case the animal is not successfully inseminated, milk production is affected.

Several biomarker measurements may be made on the animal, such as e.g. measuring levels of progesterone, LDH (Lactate Dehydrogenase), BHB (Beta-Hydroxybutyrat) and urea. Thereby important information concerning e.g. heat detection and/or pregnancy of the individual animal may be made (based on measured progesterone level), as well as mastitis (based on LDH) and ketosis (based on BHB). Also, the energy balance may be estimated (based on urea).

Thereby, a farmer/operator is provided with important information concerning each individual animal. However, to perform and analyse biomarker measurements of all individual animals at a farm is time consuming for the farmer. It also put high demands on administrative skills on the farmer to distinguish biomarker measurements from different animals; as well as high demands on cleanliness for not allowing a biomarker measurement of a first animal to be contaminated by biological matters of another animal.

It would for these reasons be advantageous for the farmer, if the taking of biomarker measurements on milk samples of different animals could be automated, and thereby minimising or at least reducing the manual work effort of the farmer.

It would be desired to find a way to assist the farmer in analysing his/her animals and enhance production at the farm.

SUMMARY

It is therefore an object of this invention to solve at least some of the above problems and facilitate for an operator to measure a biomarker value of a milk sample of an animal.

According to a first aspect of the invention, this objective is achieved by an arrangement configured to measure at least one biomarker value of a milk sample of an animal. The arrangement comprises a cassette and a service module. The cassette comprises a carrier tape comprising a plurality of test zones, which test zones are configured to indicate the biomarker value of the milk sample. The carrier tape is arranged on a first spool and a second spool, which spools are arranged to cooperate with a cassette external motor for positional adjustment of the carrier tape. The cassette in addition comprises an inspection window configured to enable inspection of the one test zone. The service module of the arrangement is configured to be connected to a milking equipment of the animal. The service module comprises a camera configured to inspect the one test zone on the carrier tape through the inspection window of the cassette. In addition, the service module also comprises at least one motor configured to be engaged with at least one of the first spool or the second spool of the cassette, in order to adjust the position of the one test zone on the carrier tape, in relation to the inspection window. Furthermore, the service module comprises a tube element configured to receive the milk sample of the animal via the milking equipment, and provide the milk sample to one of the test zones.

A biomarker, or biological marker, generally refers to a measurable indicator of some biological state or condition of the animal. The biomarker value measurement may be associated with pregnancy/reproduction of the animal.

According to a second aspect of the invention, this objective is achieved by a cassette configured to enable measurement of at least one biomarker value of a milk sample of an animal in an arrangement, according to the first aspect. The cassette comprises a carrier tape comprising a plurality of test zones, which test zones are configured to indicate the biomarker value of the milk sample. The carrier tape is arranged on a first spool and a second spool, which spools are arranged to cooperate with a cassette external motor for positional adjustment of the carrier tape. Also, in addition, the cassette comprises an inspection window, configured to enable inspection of the one test zone.

According to a third aspect of the invention, this objective is achieved by a service module configured to enable measurement of at least one biomarker value of a milk sample of an animal in an arrangement according to the first aspect. The service module comprises a camera configured to inspect one test zone on a carrier tape of a cassette, through an inspection window of the cassette. Further, the service module comprises at least one motor configured to be engaged with at least one of a first spool or a second spool of the cassette, in order to adjust the position of the one test zone on the carrier tape, in relation to the inspection window. The service module also comprises a tube element configured to receive the milk sample of the animal via a milking equipment and provide the milk sample to one of the test zones on the carrier tape.

Thanks to the described aspects, by determining biomarker values of milk samples of animals on the farm, various states, e.g. related to reproduction of the animals, or various deceases or other anomalies may be determined. By keeping the arrangement modular in form of a service module and a cassette, which may be attached to milking equipment of the farm, costs, maintenance and work intensity of the operator may be minimised or at least reduced. Also, by separating the consumable material such as measurement sticks and diluent of the cassette, from electronics and instruments of the service module; the cassette could be continuously replaced with another replacement cassette, e.g. via a courier service or postal office subscription. The service module may on the other hand be detached from the milking equipment and sent to a workshop for troubleshooting, repair, maintenance, etc. Meanwhile, an identical replacement service module may be provided to the farm, enabling continuous biomarker measurements on the farm, also when the equipment of the service module is malfunctioning. Further, the arrangement may be operated by the operator without requiring a technician to come and visit the farm. Instead, the operator may send the malfunctioning service module to the workshop.

Other advantages and additional novel features will become apparent from the subsequent detailed description.

FIGURES

Embodiments of the invention will now be described in further detail with reference to the accompanying figures, in which.

DETAILED DESCRIPTION

Embodiments of the invention described herein are defined as an arrangement, a cassette and a service module, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1:
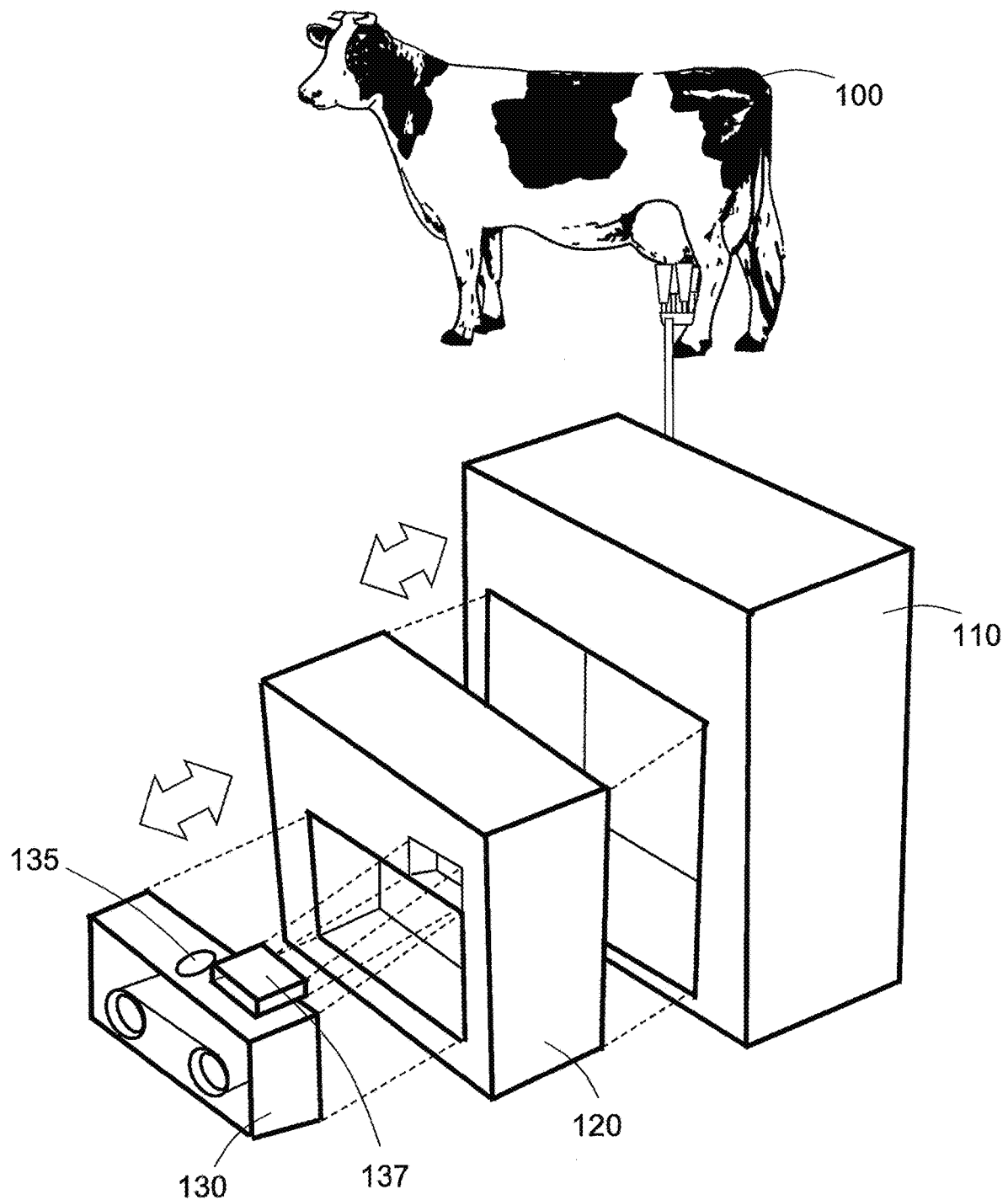
FIG. 1 illustrates an example of an arrangement for measuring a biomarker value of a milk sample of an animal.

FIG. 1 illustrates a scenario with an animal 100 which may be comprised in a herd of dairy animals at a dairy farm. "Animal" may be any arbitrary type of domesticated female milk producing and/or meat producing mammal such as cow, goat, sheep, horse, camel, dromedary, primate, dairy buffalo, donkey, reindeer, yak, etc.

Milk of the animal 100 may be extracted by a milking equipment 110 such as e.g. a milking robot or other milking arrangement, and provided to a service module 120.

The service module 120 may be releasably inserted into the milking equipment 110 in some embodiments. Thus, there may be an interface between the milking equipment 110 and the service module 120 for providing milk and possibly electricity via the milking equipment 110 to the service module 120.

The service module 120 comprises various electronics and equipment such as a camera, one or several pumps, a tube element for attachment to the interface to the milking equipment 110, motors, a communication unit etc.

A cassette 130 may be detachably inserted into the service module 120. The cassette 130 comprises test zones configured to indicate a biomarker value of a milk sample of the animal 100.

Thereby, a milk sample of the animal 100 may be extracted from the animal 100 by the milking equipment 110 and provided via the service module 120 to the test zone of the cassette 130. The test zone may react on presence and/or amount of one or several biomarkers, e.g. by changing colours. The camera in the service module 120 may capture an image through an inspection window 135 in the cassette 130. The captured image of the test zone may then be analysed by a control unit. The presence and/or quantity of the biomarker in the milk sample may thereby be determined.

The measured biomarker may be e.g. progesterone, glycoprotein, oestrogen and/or Gonadatropin-Releasing Hormones, or any other similar biomarker associated with reproduction of the animal 100, in different embodiments.

Progesterone is a hormone that regulates several physiological functions of the animal 100. Progesterone may prepare the uterus for pregnancy, maintain the pregnancy if fertilisation occurs, and inhibit the animal 100 from showing signs of standing oestrus and ovulating when pregnant. Progesterone levels, for example, may rise at the beginning of the pregnancy, and be kept at a high level throughout the pregnancy of the animal 100. Progesterone levels in milk samples may be used to monitor pregnancy, oestrous cycles (heat detection) and/or postpartum ovarian activity. For these reasons, progesterone levels of animals 100 at the farm is interesting for the operator to detect and keep track of.

However, the measured biomarker may in some embodiments comprise LDH (Lactate Dehydrogenase), BHB (Beta-HydroxyButyrat), urea, somatic cell count, and/or milk yield; or other biomarker related to status of the animal 100. In some embodiments, a plurality of the above enumerated biomarkers may be measured. Alternatively, in some embodiment, the operator may subscribe to a cassette 130 comprising a certain test zone on a carrier tape configured to measure a biomarker, or a set of biomarkers, as selected by the farmer; and/or different cassettes 130 comprising test zones on the carrier tape configured to measure different biomarkers, or sets of biomarkers, during different periods of time.

In some embodiments, a second cassette 137 may also be detachably inserted into the service module 120. The second cassette 137 may comprise for example a diluent container with diluent, a needle, and/or one or several pumps.

Figure 2:
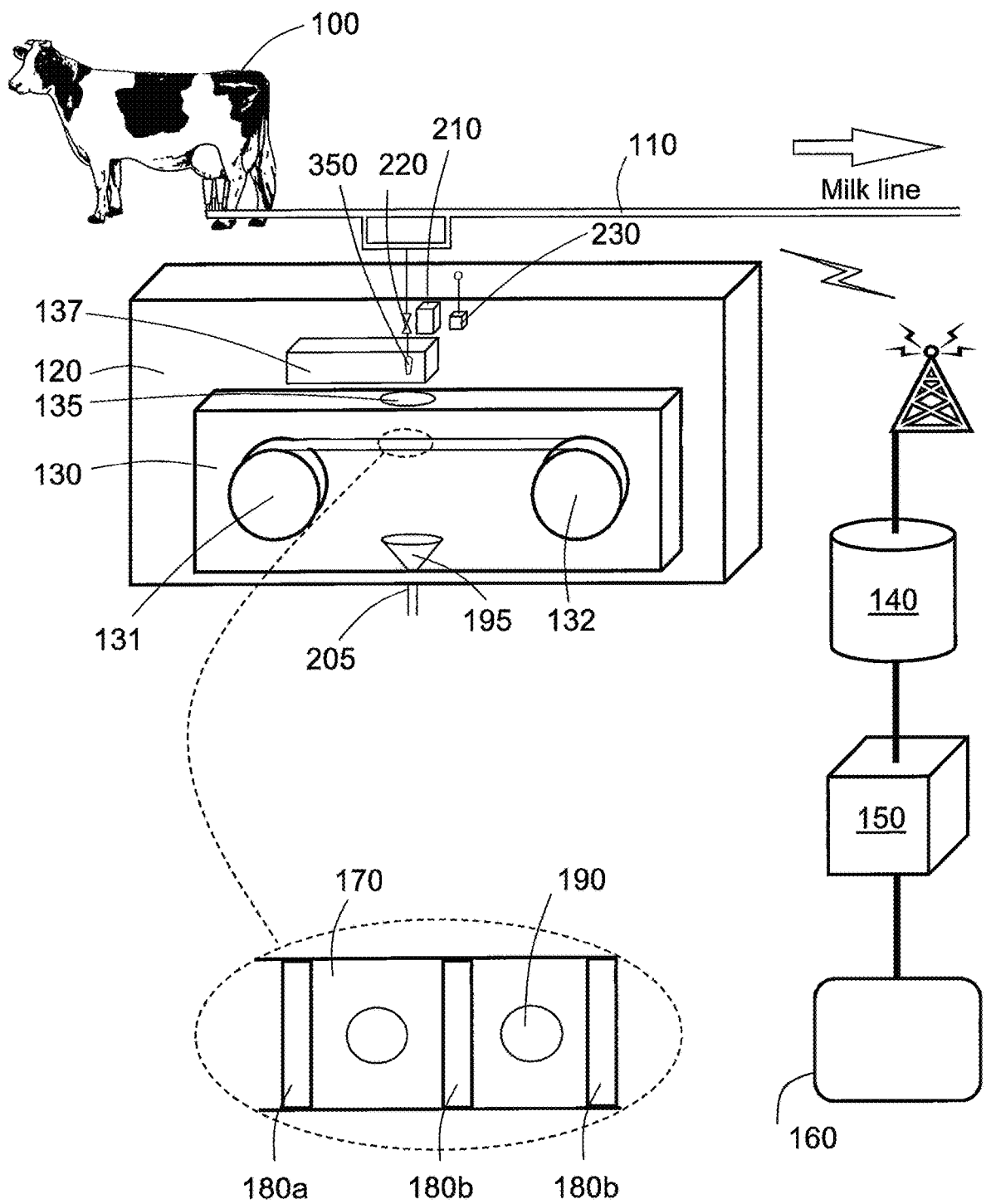
FIG. 2 illustrates a cassette inserted into a service module, according to an embodiment.

FIG. 1 and FIG. 2 depict general overviews of the provided solution, without going too much into details, in order for the reader to get a rough overview. Sublime examples of details of the involved entities, in particular the service module 120 and the cassette 130, and how they interact with each other may be fully enjoyed in FIG. 3A, FIG. 3B and FIG. 4.

FIG. 2 illustrates a scenario illustrating a service module 120, a cassette 130, and a second cassette 137, according to an embodiment. The service module 120 comprises electronics and equipment such as e.g. a camera 210, a tube element 220 for attachment to the interface to the milking equipment 110, a motor, a communication unit 230, etc., to be used for determining a biometric value of a milk sample received from an animal 100. In some embodiments, the service module 120 may comprise one or several pumps configured to act on the tube element 220 for advancing the milk sample through the tube element 220.

In the illustrated embodiment, the second cassette 137 may comprise a needle 350 for applying the milk sample to a test zone on a carrier tape in the cassette 130 through the inspection hole 135 in the cassette 130. The camera 210 may then align the needle 350 with the test zone on the carrier tape of the cassette 130. The second cassette 137 may also comprise a diluent container, configured to contain diluent to be mixed with the milk sample.

Figure 3A:
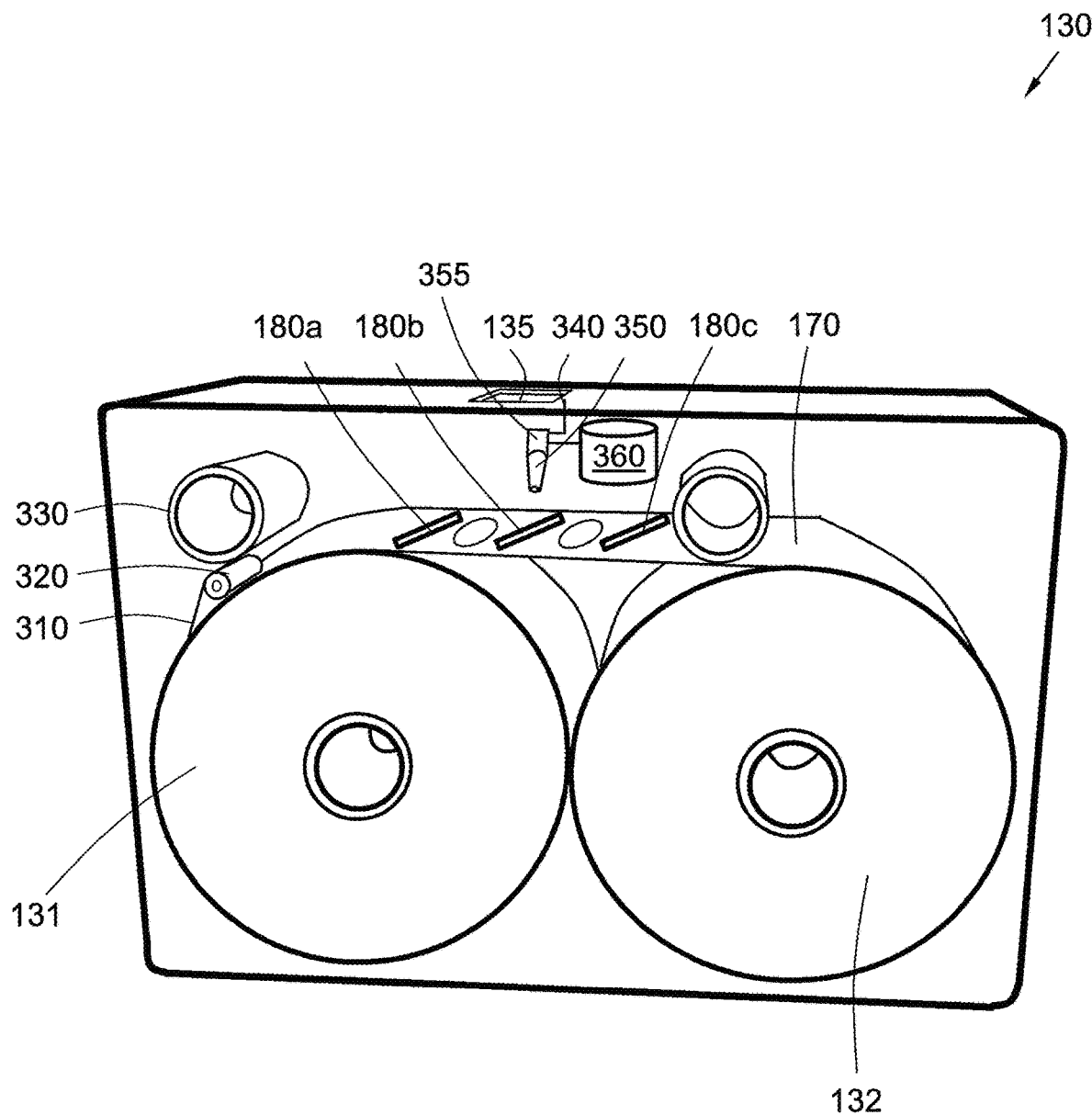
FIG. 3A illustrates a cassette, according to an embodiment.
Figure 3B:
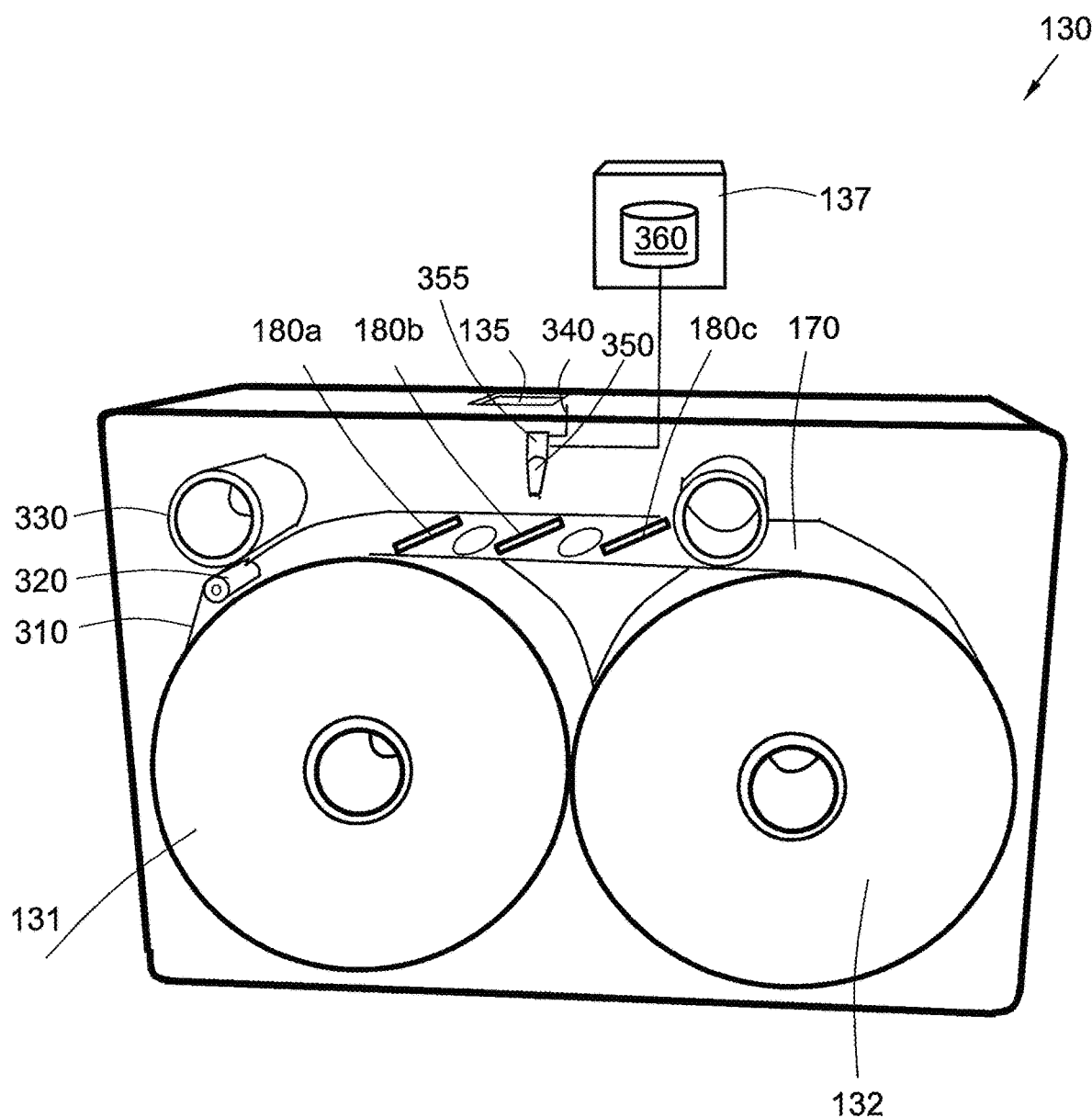
FIG. 3B illustrates a cassette and a second cassette, according to an embodiment.

However, in other embodiments, the needle 350 may be comprised in the service module 120; or in the cassette 130, as will be further exemplified in FIG. 3A and FIG. 3B.

The communication unit 230 may communicate via a wired or wireless communication interface, with a control unit 150, a database 140, and/or an output unit 160.

Such wireless communication interface may comprise, or at least be inspired by wireless communication technology such as Wi-Fi, Wireless Local Area Network (WLAN), Ultra Mobile Broadband (UMB), Bluetooth (BT) to name but a few possible examples of wireless communications in some embodiments. The communication may alternatively be made over a wireless interface comprising, or at least being inspired by radio access technologies such as e.g. 3GPP LTE, LTE-Advanced, E-UTRAN, UMTS, GSM, GSM/EDGE, WCDMA, Time Division Multiple Access (TDMA) networks, Frequency Division Multiple Access (FDMA) networks, Orthogonal FDMA (OFDMA) networks, Single-Carrier FDMA (SC-FDMA) networks, Worldwide Interoperability for Microwave Access (WiMax), or Ultra Mobile Broadband (UMB), High Speed Packet Access (HSPA) Evolved Universal Terrestrial Radio Access (EUTRA), Universal Terrestrial Radio Access (UTRA), GSM EDGE Radio Access Network (GERAN), 3GPP2 CDMA technologies, e.g., CDMA2000 1×RTT and High Rate Packet Data (HRPD), or similar, just to mention some few options, via a wireless communication network.

The control unit 150 is configured to determine a biomarker value of the milk sample of the animal 100, based on an analysis of the image, captured by the camera 210. The control unit 150 may be comprised in the service module 120 in some embodiments; or be external to the service module 120.

The database 140 may store measured biometric values of the animal 100, associated with an identity reference of the animal 100 and/or a time stamp of the measurement. Other measurements and/or data related to the animal 100 may also be stored in the database 140, such as milk yield, e.g. measured by the milk flow meter 135a, 135b, 135c, activity, breed, parity, rumination, lactation, resting, feed intake, energy balance, Days In Milk, milk production, age and possibly other similar animal status related parameters.

The output unit 160 may be e.g. a cellular mobile telephone, a stationary or portable computing device, a computer tablet, a display, a pair of intelligent glasses, a smart contact lens, an augmented reality device, a smart watch or similar device having a user interface and wireless communication ability.

Via the output unit 160, an operator may take part of the result of the biomarker measurement of the milk sample. The operator is thereby able to analyse the status of the animal 100, such as e.g. if the animal 100 is in heat, in case progesterone is measured.

When a deviation, exceeding a first threshold limit, is detected between the outcomes of the biomarker measurement and the corresponding reference value, an alert may be outputted to the operator. The alert may comprise e.g. visual information, an audio message, a tactile signal or a combination thereof, encouraging the operator to further investigate the reasons for the detected deviation in result. In case a plurality of people is working with the herd, a broadcast may be made to the plurality of operators and their respective associated output units 160, in some embodiments.

The operator may be e.g. a farmer or other person working at a farm; or a veterinarian, agronomist, dietician, biologist, zoologist, ecologist, mammologist, domestic animal researcher, zookeeper or other similar human, temporarily, accidently or permanently visiting the farm. The "farm" as the term herein is used may be a barn, a ranch, a stable or other similar agricultural structure for keeping animals.

The cassette 130 is releasably inserted into the service module 120. The cassette 130 comprises a carrier tape 170, which in turn comprises a plurality of test zones 180a, 180b, 180c.

The carrier tape 170 is arranged on a first spool 131 and a second spool 132, which spools 131, 132 are arranged to cooperate with a cassette external motor for positional adjustment of the carrier tape 170. The cassette external motor may be comprised in the service module 120 in some embodiments. The camera 210 of the service module 120 may capture an image of the test zones 180a, 180b, 180c of the carrier tape 170 through the inspection window 135, and based on these images, the cassette external motor may adjust the carrier tape 170 for positioning a new test zone 180a, 180b, 180c, on which a new test is to be made, in relation to a needle 350.

The needle 350, which may be comprised e.g. in the service module 120, in the cassette 130, or in the second cassette 137, may be adjustable in some embodiments. For example, the needle 350 may comprise a drop guide with adjustable diameter. Alternatively, drop guides of different diameters may be interchangeably applied to the needle. The concept of the needle 350 is to be interpreted broadly, e.g. as an opening or tubing for providing a received milk sample, or a subset thereof, to a test zone 180a, 180b, 180c.

The test zones 180a, 180b, 180c are configured to indicate the biomarker value of the milk sample, when the milk sample is applied on one of the test zones 180a, 180b, 180c. The test zones 180a, 180b, 180c may be designed for one time usage each. In some embodiments, the test zones 180a, 180b, 180c of the carrier tape 170 may be configured to change colour when exposed to the biomarker. The test zones 180a, 180b, 180c may be based on dry stick technology in some embodiments.

The camera 210 in the service module 120 may capture an image of the test zone 180a, 180b, 180c in question, after a predetermined or configurable time period. The colour of the test zone 180a, 180b, 180c on the captured image may then be analysed by the control unit 150, e.g. by a comparison with a colour chart where different colours or nuances are associated with a certain biomarker level of the milk sample.

The cassette 130 also may comprises a liquid insertion connection in some embodiments, configured to receive the milk sample of the animal 100 from the tube element 220 of the service module 120. Further, the cassette 130 may comprise the needle 350, configured to receive the milk sample of the animal 100 via the liquid insertion connection and apply the milk sample to one of the test zones 180a, 180b, 180c on the carrier tape 170.

The milk sample may in some embodiments be mixed with a diluent before being applied to the test zone 180a, 180b, 180c on the carrier tape 170. The diluent may in some embodiments be kept in a diluent container comprised in the cassette 130. In other embodiments, the diluent container may be comprised in a second cassette 137, different from the cassette 130 comprising the carrier tape 170; or in a separate diluent container external to the cassette 130.

An advantage with having the diluent container comprised in the cassette 130 is that the operator only is required to replace the cassette 130 for a new one when all the test zones 180a, 180b, 180c on the carrier tape 170 and the diluent have been used. The amount of diluent in the container of the cassette 130 may thus be adjusted to the number of test zones 180a, 180b, 180c on the carrier tape 170, thereby simplifying and reducing the amount of work the operator has to spend on maintenance of the arrangement.

In embodiments, wherein the diluent is kept in a separate container in a separate cassette, such as the second cassette 137, the operator may change the respective cassettes 130, 137 at different time intervals. In a non-limiting example, the cassette 130 may be changed once a month while the second cassette 137 comprising the diluent container and the needle 350 may be changed twice a year. In case the diluent is kept in a container external to the cassette 130, the operator may refill the diluent, which may reduce overall costs of the operator. Yet an advantage by having multiple cassettes 130, 137 is that in case a fabrication error or a transportation damage occur of a therein comprised entity, such as e.g. the needle 350, only that particular cassette 130, 137 comprising the defect entity has to be exchanged, which saves resources.

In some embodiments, the cassette 130 may comprise at least one pump configured to act on the tube element 220 for providing the milk sample to the needle 350. The at least one pump may alternatively be comprised in the second cassette 137 in embodiments wherein the diluent is comprised in the second cassette 137.

The ratio of milk and diluent may be adjusted by changing the respective pump speed of one or both liquids, i.e. milk/diluent respectively, in case each liquid is associated with a respective pump.

The needle 350 comprised in the cassette 130, in the second cassette 137, or the service module 120 may comprise a mixing chamber configured to mix obtained diluent with the milk sample before applying the mixed milk sample to the one test zone 180a, 180b, 180c, in some embodiments.

The carrier tape 170 of the cassette 130 may in some embodiments comprise a flush hole 190. To distinguish the milk samples of the different animals 100, it may be avoided that milk from a previously milked animal 100 remains in the tubing of the service module 120, the cassette 130 and/or the second cassette 137 by flushing the respective tubing with milk of the animal 100, from which a new sample is to be taken. The carrier tape 170 may then be forwarded so that milk from the animal 100 could be flushed via the flush hole 190, before the carrier tape 170 again is forwarded for putting the test zone 180a, 180b, 180c in position for receiving a milk sample from the subsequently following animal.

The milk provided to the cassette 130, either, possibly, for the milk sample applied on the test zones 180a, 180b, 180c, or the milk flushed through the flush hole 190, may be evacuated from the cassette 130 via an aperture 195 of the cassette 130, and a drainage 205 of the service module 120. The evacuated milk may in some embodiments be returned back to the milk line; in other embodiments, the evacuated milk may be dissipated to a sewer or otherwise further evacuated from the farm.

In some embodiments, the cassette 130 and/or the second cassette 137 may be sealed from the environment and thereby create a climate chamber, wherein a climate environment prevails in the cassette 130/second cassette 137. The cassette 130/second cassette 137 thereby becomes isolated from environmental impact of dust, dirt, liquids, etc., of the farm.

The cassette 130, in some embodiments, may comprise a sealing tape configured to seal the plurality of test zones 180a, 180b, 180c on the carrier tape 170. The sealing tape may be a foil which is heat sealed to the carrier tape 170. The reason is that it is important that milk from a first animal 100 does not soak a test zone 180a, 180b, 180c on which a subsequent animal is to use for biomarker test, as the milk from the first animal may contaminate the test zone 180a, 180b, 180c of the second animal. For this reason, the cassette 130 may further comprise a de-sealer, configured to remove the sealing tape from the one test zone 180a, 180b, 180c when the one test zone 180a, 180b, 180c is adjusted into a position aligned with the needle 350.

An advantage of the disclosed solution, by making a division between a service module 120 comprising camera, motor, pumps and other electronics and/or apparatuses; and one or several cassettes 130, 137 comprising disposable material, the solution becomes very easy to use for the operator.

The cassette 130 may comprise test zones 180a, 180b, 180c etc., for supporting the farm for a certain predetermined period of time, such as e.g. a month, two months, etc. Before the end of that time period, a supplier may provide a new cassette 130 to the farm, which the operator easy may put into the service module 120, without having to interact with the sensible electronics of the service module 120. The used cassette 130 may then be disposed.

In case a hardware failure or other malfunction occur, the operator may remove the service module 120 from the milking equipment 110 (and also remove the cassette 130 from the service module 120) and provide the service module 120 to a service supplier for reparation/adjustment. During the time period the service module 120 is on repair, the operator may borrow another service module 120 from the service supplier. Thereby, biomarker values of the animals 100 may be determined without interruptions, also when the service module 120 or any part thereof is malfunctioning. Also, as no external technician is required to visit the farm, neither for changing the disposable cassettes 130, 137, nor for analysing errors in the service module 120, costs for service and maintenance are minimised or at least reduced.

FIG. 3A illustrates a cassette 130 according to an embodiment.

A carrier tape 170 comprising a plurality of test zones 180a, 180b, 180c configured to measure at least one biomarker value of a milk sample. The carrier tape 170 is arranged on a first spool 131 and a second spool 132. In the illustrated embodiment, the carrier tape 170 is covered with a sealing tape 310 configured to seal the plurality of test zones 180a, 180b, 180c on the carrier tape 170.

Also, in the illustrated embodiment, a de-sealer 320 is comprised, for removing the sealing tape 310 from the test zone 180a, 180b, 180c on the carrier tape 170 when the one test zone 180a, 180b, 180c is adjusted into a position aligned with a needle 350.

The cassette 130, as already discussed, may comprise a liquid insertion connection 340 configured to receive the milk sample of the animal 100. The optional liquid insertion connection 340 thus constitute a connection interface between the cassette 130 and the service module 120, through which the milk sample may be received via a tube element 220 of the service module 120 in embodiments wherein the needle 350 is comprised in the cassette 130.

The cassette 130 may also comprise a needle 350. The needle 350 may be configured to receive the milk sample of the animal 100 and apply the milk sample to one of the test zones 180a, 180b, 180c on the carrier tape 170.

In some embodiments, wherein the needle 350 is comprised in the cassette 130, the cassette 130 may comprise at least one pump, configured to act on the tube element 220 for providing the milk sample to the needle 350.

The needle 350 may comprise a chamber 355 for mixing the received milk sample with diluent, which in the illustrated embodiment is kept in a diluent container 360 in the cassette 130.

When the carrier tape 170 is moved for placing the test zone 180a, 180b, 180c to be used in position aligned with the needle 350, the milk/diluent mix may be applied on the test zone 180a, 180b, 180c.

FIG. 3B illustrates a cassette 130 and a second cassette 137, according to an embodiment. The illustrated embodiment shares various similarities with the already discussed embodiment in FIG. 3A; however, the diluent container 360 is comprised in a second cassette 137, which is distinct from the cassette 130.

An advantage with having separate cassettes 130, 137, one first cassette 130 for the carrier tape/test zones 180a, 180b, 180c and one second cassette 137 for maintaining the diluent in a diluent container 360 is that the respective cassettes 130, 137 may be exchanged with different time intervals, e.g. the first cassette 130 may be replaced once a month while the second cassette 137 may be replaced every second months; or vice versa. Thereby, an increased flexibility is achieved, enabling an adaption of the arrangement as a whole to the particular circumstances and herd size on the farm.

The needle 350 is comprised in the cassette 130 in the illustrated embodiment. However, as already discussed, the needle 350 may be comprised in the second cassette 137; or in the service module 120.

In a non-limiting example, the diluent of the diluent container 360 in the second cassette 137 may be supplied to a plurality of cassettes 130 at the farm.

Figure 4:
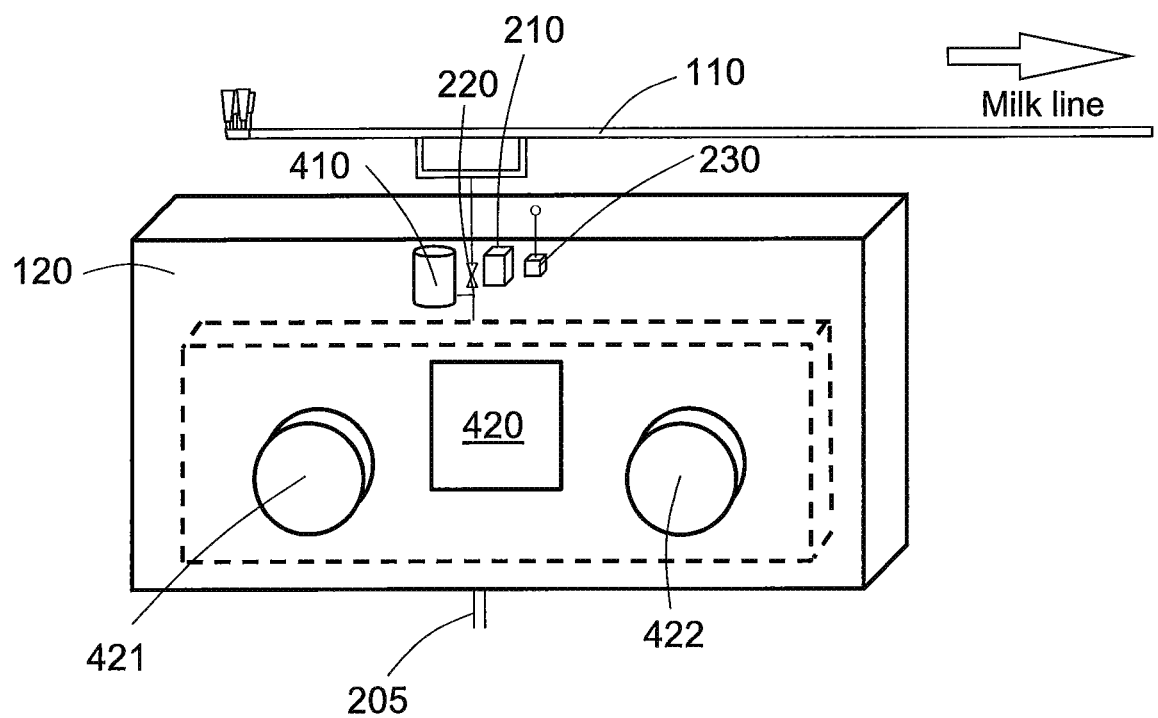
FIG. 4 illustrates a service module according to an embodiment.

FIG. 4 illustrates a service module 120, substantially as previously presented, configured to enable measurement of at least one biomarker value of a milk sample of an animal 100 in an arrangement 400, in cooperation with a cassette 130.

The service module 120 comprises a camera 210 configured to inspect one test zone 180a, 180b, 180c on a carrier tape 170 of a cassette 130, through an inspection window 135 of the cassette 130. The camera 210 may comprise e.g. a Charge-Coupled Device (CCD), an Active-Pixel Sensor (APS), a Complementary Metal-Oxide-Semiconductor (CMOS) sensor or other similar arrangement in different embodiments.

Further, the service module 120 comprises at least one motor 420 configured to be engaged with at least one of a first spool 131 or a second spool 132 of the cassette 130, in order to adjust the position of the one test zone 180a, 180b, 180c on the carrier tape 170, in relation to the inspection window 135. The motor 420 may propel a first rotary driving means 421 and/or a second rotary driving means 422; which first rotary driving means 421 and/or second rotary driving means 422 may interact with a first spool 131 and/or a second spool 132 of the cassette 130, whereon a carrier tape 170 is arranged. The motor 420 may then adjust the position of the one test zone 180a, 180b, 180c on the carrier tape 170, in relation to the inspection window 135 of the cassette 130 by rotating the first spool 131 and/or the second spool 132 of the cassette 130 with the first rotary driving means 421 and/or second rotary driving means 422. The needle 350 and the position of the test zone 180a, 180b, 180c on the carrier tape 170 may thereby be aligned, based on images captured by the camera 210 through the inspection window 135.

The motor 420 may comprise an electric motor, such as e.g. an Alternating Current (AC) motor 420 in some embodiments. The currency may be supported from an external source of energy. In some embodiments, the motor 420 may be a Direct Currency (DC) motor 420.

Further, the service module 120 also comprises a tube element 220 configured to receive the milk sample of the animal 100 via a milking equipment 110 and provide the milk sample to a needle 350, e.g. a needle 350 comprised in the cassette 130, or alternatively in the second cassette 137, via a liquid insertion connection 340 of the cassette 130.

Thereby, there may be an interface between the service module 120 and the cassette 130 and/or the second cassette 137, wherein the tube element 220 is connected to the liquid insertion connection 340 of the cassette 130 and/or the second cassette 137.

The service module 120 may in addition comprise at least one pump 410 in some embodiments, configured to act on the tube element 220 for providing the milk sample to the needle 350. The pump 410 may thus act on the tube element 220 to get the milk sample to propagate through the tube element 220, e.g. via the liquid insertion connection 340 of the cassette 130 to reach the needle 350; or rather the mixing chamber 355 of the needle 350.

Further, the service module 120 may comprise a drainage 205 arranged to receive liquid evacuated from the cassette 130 via an aperture 195 of the cassette 130, and to evacuate the liquid from the service module 120.

Figure 5:
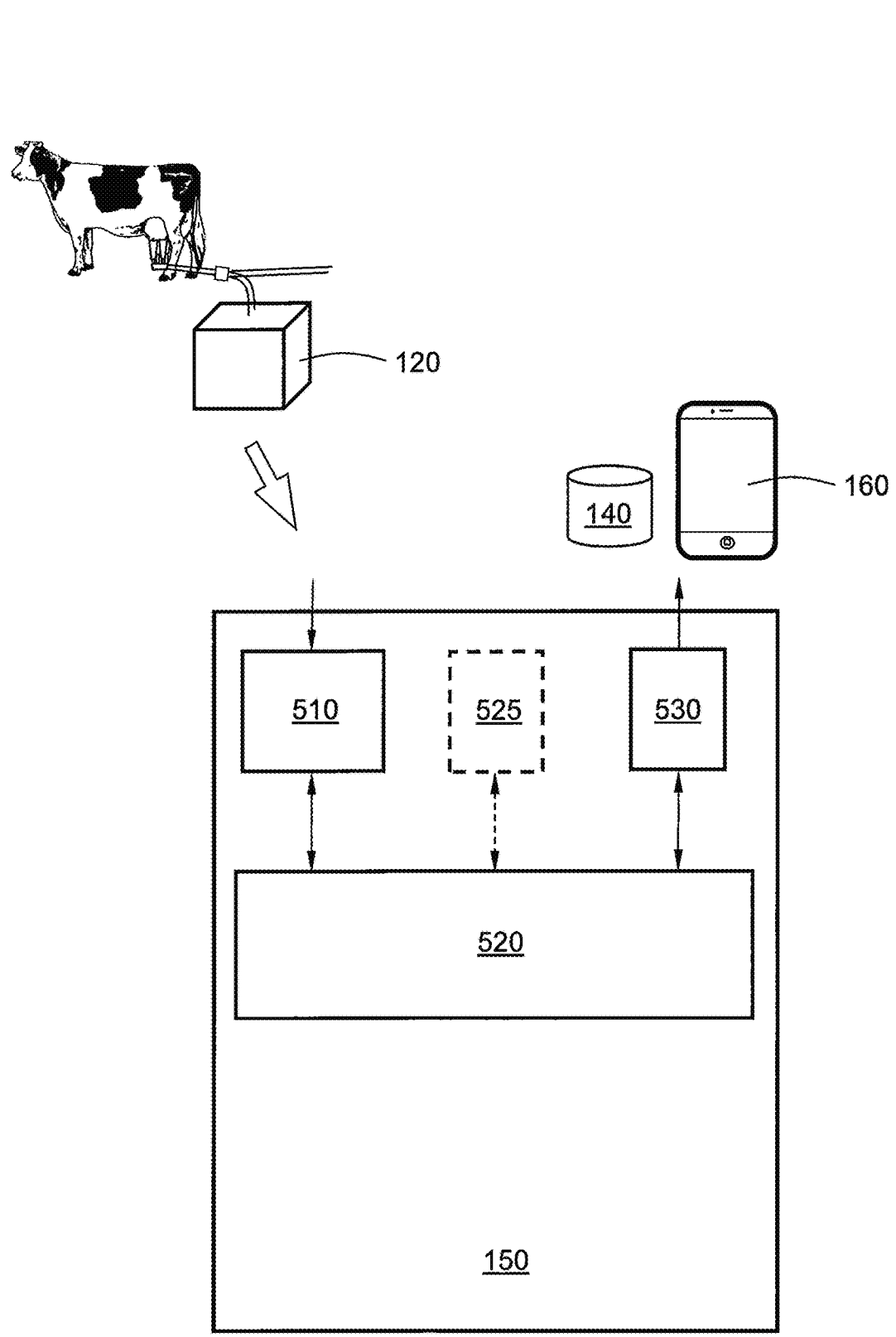
FIG. 5 is an illustration depicting an arrangement.

FIG. 5 illustrates an arrangement 500 for measuring at least one biomarker value of a milk sample of an animal 100.

The arrangement 500 comprises a cassette 130. The cassette 130 comprises a carrier tape 170 comprising a plurality of test zones 180a, 180b, 180c, which test zones 180a, 180b, 180c are configured to indicate the biomarker value of the milk sample. The carrier tape 170 is arranged on a first spool 131 and a second spool 132, which spools 131, 132 are arranged to cooperate with a cassette external motor 420 for positional adjustment of the carrier tape 170.

The carrier tape 170 of the cassette 130 may comprise a flush hole 190 between each test zone 180a, 180b, 180c on the carrier tape 170, in some embodiments.

The cassette 130 may also comprise a liquid insertion connection 340 configured to receive the milk sample of the animal 100, in some embodiments.

Further, the cassette 130 in addition may comprise a needle 350 configured to receive the milk sample of the animal 100 via the liquid insertion connection 340 and apply the milk sample to one of the test zones 180a, 180b, 180c. The cassette 130 also comprises an inspection window 135 configured to enable inspection of the one test zone 180a, 180b, 180c.

The optional needle 350 of the cassette 130 may alternatively comprise a mixing chamber 355 configured to mix obtained diluent with the milk sample before applying the mixed milk sample to the one test zone 180a, 180b, 180c.

The cassette 130 may in some embodiments be configured to be detachably inserted in a service module 120 and held in place by a fastening means such as a snap lock, a magnet, a screw, etc.

In some embodiments, the cassette 130 may also comprise a sealing tape 310 configured to seal the plurality of test zones 180a, 180b, 180c on the carrier tape 170. Further, the cassette 130 may comprise a de-sealer 320 configured to remove the sealing tape 310 from the one test zone 180a, 180b, 180c when the one test zone 180a, 180b, 180c is adjusted into a position aligned with the needle 350.

The cassette 130 may in some embodiments prevail a climate environment, created by an environmental isolation between the cassette 130 and the environment. Thereby, the test zones 180a, 180b, 180c on the carrier tape 170 may be protected from non-intentional impact from external factors such as milk from unknown animals, dust, dirt, etc.

In some embodiments, the cassette 130 also may comprise a diluent container 360 configured to contain diluent to be mixed with the milk sample.

Further, the cassette 130 of the arrangement 500 also may comprise an aperture 195, arranged to evacuate liquid from the cassette 130.

The arrangement 500 also comprises a service module 120. The service module 120 is configured to be connected to a milking equipment 110 of the animal 100. The service module 120 comprises a camera 210 configured to inspect the one test zone 180a, 180b, 180c on the carrier tape 170 through the inspection window 135 of the cassette 130. Further, the service module 120 also comprises at least one motor 420 configured to be engaged with at least one of the first spool 131 or the second spool 132 of the cassette 130, in order to adjust the position of the one test zone 180a, 180b, 180c on the carrier tape 170, in relation to the inspection window 135.

The motor 420, according to some embodiments, may be configured to adjust the position of the one test zone 180a, 180b, 180c on the carrier tape 170, based on an alignment of the needle 350 and the one test zone 180a, 180b, 180c. The alignment may be supervised by the camera 210 through the inspection window 135 of the cassette 130.

Also, the service module 120 comprises a tube element 220 configured to receive the milk sample of the animal 100 via the milking equipment 110, and provide the milk sample to the needle 350 of the cassette 130 via the liquid insertion connection 340 of the cassette 130 in some embodiments. In other embodiments, wherein the needle 350 is comprised in the service module 120, the milk sample may be provided by the needle 350 via the inspection window 135 of the cassette 130.

The arrangement 500 may in some embodiments comprise at least one pump 410 configured to act on the tube element 220 for providing the milk sample to the needle 350. The pump 410 may be comprised in the service module 120 or in the cassette 130 in different embodiments.

The service module 120 may in some embodiments be configured to be detachably inserted in the milking equipment 110.

The arrangement 500 may furthermore in some alternative embodiments comprise a second cassette 137, comprising a diluent container 360 configured to contain diluent to be mixed with the milk sample, and/or the needle 350.

Further, the service module 120 may comprise a drainage 205 arranged to receive liquid evacuated from the cassette 130 via the aperture 195 of the cassette 130, and to evacuate the liquid from the service module 120, according to some embodiments.

The service module 120 may also comprise a communication device 230, configured to communicate an image captured by the camera 210 of the service module 120, with the control unit 150.

The arrangement 500 may also comprise a control unit 150 configured to analyse a captured image of the one test zone 180a, 180b, 180c, captured by the camera 210, in some embodiments.

Further, the arrangement 500 may comprise a database 140 configured to store an analysis of the biomarker value of the milk sample of the animal 100 with an identity of the animal 100. The arrangement 500 may furthermore comprise an output device 160 configured to output a result of the measured biomarker value of the milk sample.

The optional control unit 150 may comprise a receiver 510 configured to receive information from the service module 120, such as biomarker measurement values of animals 100 of the herd.

The control unit 150 also comprises a processing circuitry 520 configured for performing various calculations for conducting a computer program.

Such processing circuitry 520 may comprise one or more instances of a processing circuit, i.e. a Central Processing Unit (CPU), a processing unit, a processing circuit, a processor, an Application Specific Integrated Circuit (ASIC), a microprocessor, or other processing logic that may interpret and execute instructions. The herein utilised expression "processor" may thus represent a processing circuitry comprising a plurality of processing circuits, such as, e.g., any, some or all of the ones enumerated above.

Furthermore, the control unit 150 may comprise a memory 525 in some embodiments. The optional memory 525 may comprise a physical device utilised to store data or programs, i.e., sequences of instructions, on a temporary or permanent basis. According to some embodiments, the memory 525 may comprise integrated circuits comprising silicon-based transistors. The memory 525 may comprise e.g. a memory card, a flash memory, a USB memory, a hard disc, or another similar volatile or non-volatile storage unit for storing data such as e.g. ROM (Read-Only Memory), PROM (Programmable Read-Only Memory), EPROM (Erasable PROM), EEPROM (Electrically Erasable PROM), etc. in different embodiments.

Further, the control unit 150 may comprise a signal transmitter 530. The signal transmitter 530 may be configured for transmitting signals via a wired or wireless communication interface to the output unit 160 of the operator, possibly via a transceiver; and/or to the database 140.

Furthermore, a computer program comprising instructions to perform sequential biometric measurements on test zones 180a, 180b, 180c on the carrier tape 170 of the cassette 130 of milk samples obtained from animals 100 may be performed in the control unit 150.

The computer program mentioned above may be provided for instance in the form of a computer-readable medium, i.e. a data carrier carrying computer program code for performing at least some of the computer program steps, according to some embodiments when being loaded into the one or more processing circuitries 520 of the control unit 150. The data carrier may be, e.g., a hard disk, a CD ROM disc, a memory stick, an optical storage device, a magnetic storage device or any other appropriate medium such as a disk or tape that may hold machine readable data in a non-transitory manner. The computer program may furthermore be provided as computer program code on a server and downloaded to the control unit 150 remotely, e.g. over an Internet or an intranet connection.

The embodiments, or parts thereof, illustrated in FIG. 1, FIG. 2, FIG. 3A, FIG. 3B, FIG. 4 and/or FIG. 5 may with advantage be combined with each other for achieving further benefits.

The terminology used in the description of the embodiments as illustrated in the accompanying drawings is not intended to be limiting of the described arrangement 500, cassette 130, service module 120, control unit 150, second cassette 137 and/or computer program. Various changes, substitutions and/or alterations may be made, without departing from invention embodiments as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims. The mere fact that certain measures or features are recited in mutually different dependent claims, illustrated in different figures or discussed in conjunction with different embodiments does not indicate that a combination of these measures or features cannot be used to advantage. A computer program may be stored/distributed on a suitable medium, such as an optical storage medium or a solid-state medium supplied together with or as part of other hardware, but may also be distributed in other forms such as via Internet or other wired or wireless communication system.

The invention claimed is:

1. An arrangement configured to measure at least one biomarker value of a milk sample of an animal, the arrangement comprising:
   a cassette comprising:
      a carrier tape comprising a plurality of test zones configured to indicate the biomarker value of the milk sample, the carrier tape being disposed on a first spool and a second spool, the first and second spools being configured to cooperate with a cassette external motor for positional adjustment of the carrier tape, and
      an inspection window configured to enable inspection of one of the test zones;
   a service module configured to be connected to a milking equipment of the animal and configured to receive the cassette therein, the cassette being detachably inserted into the service module, the service module comprising:
      a camera configured to inspect the one test zone on the carrier tape through the inspection window of the cassette and to capture images of the one test zone,
      at least one motor configured to be engaged with at least one of the first spool and the second spool of the cassette, in order to adjust the position of the one test zone on the carrier tape in relation to the inspection window,
      a tube element configured to receive the milk sample of the animal via the milking equipment and configured to provide the milk sample to one of the test zones,
      a needle configured to receive the milk sample of the animal and apply the milk sample to one of the test zones, and
      at least one pump configured to act on the tube element to provide the milk sample to the needle; and
   a controller connected to the service module, the controller being configured to control the at least one motor to adjust the position of the one test zone on the carrier tape, based on the captured images of the one test zone and to align the needle and the one test zone, alignment of the needle and the one test zone being supervised by the same camera through the inspection window of the cassette,
   wherein the captured images are used to determine the presence of the at least one biomarker value of the milk sample.

2. The arrangement according to claim 1, wherein the service module is configured to be detachably inserted in the milking equipment.

3. The arrangement according to claim 1, wherein the cassette further comprises:
   a liquid insertion connection configured to receive the milk sample of the animal.

4. The arrangement according to claim 1, wherein the cassette further comprises:
   a sealing tape configured to seal the plurality of test zones on the carrier tape, and
   a de-sealer configured to remove the sealing tape from the one test zone when the one test zone is adjusted into a position aligned with the needle.

5. The arrangement according to claim 1, wherein the cassette further comprises: a diluent container configured to contain diluent to be mixed with the milk sample.

6. The arrangement according to claim 1, further comprising another cassette comprising:
   a diluent container configured to contain diluent to be mixed with the milk sample.

7. The arrangement according to claim 6, wherein the other cassette comprises
   a liquid insertion connection configured to receive the milk sample of the animal, and
   another needle configured to receive the milk sample of the animal via the liquid insertion connection and apply the milk sample to one of the test zones.

8. The arrangement according to claim 1, wherein the needle comprises a mixing chamber configured to mix obtained diluent with the milk sample before applying the mixed milk sample to the one test zone.

9. The arrangement according to claim 1, wherein the cassette further comprises an aperture configured to evacuate liquid from the cassette, and
   the service module further comprises a drainage configured to receive liquid evacuated from the cassette via the aperture of the cassette, and to evacuate the liquid from the service module.

10. The arrangement according to claim 1, wherein the carrier tape of the cassette comprises a flush hole between at least two of the test zones on the carrier tape.

11. The arrangement according to claim 1, wherein the controller is configured to analyze a captured image of the one test zone, captured by the camera, and
    the arrangement further comprises
       a database configured to store an analysis of the biomarker value of the milk sample of the animal with an identity of the animal; and
       an output device configured to output a result of the measured biomarker value of the milk sample,
    wherein the service module further comprises a communication device configured to communicate an image captured by the camera of the service module with the controller.

* * * * *